United States Patent
Hinzpeter et al.

(10) Patent No.: US 7,981,352 B2
(45) Date of Patent: Jul. 19, 2011

(54) METHOD AND APPARATUS FOR QUALITY SURVEILLANCE DURING THE MANUFACTURE OF TABLETS

(75) Inventors: Jürgen Hinzpeter, Schwarzenbek (DE); Ingo Schmidt, Schwarzenbek (DE); Ulrich Gathmann, Hamburg (DE); Jörg Gaedecke, Geesthacht (DE); Werner Seifert, Wentorf (DE)

(73) Assignee: Fette GmbH, Schwarzenbak (DE)

( * ) Notice: Subject to any disclaimer, the term of this patent is extended or adjusted under 35 U.S.C. 154(b) by 947 days.

(21) Appl. No.: 11/038,104

(22) Filed: Jan. 21, 2005

(65) Prior Publication Data
US 2005/0184435 A1    Aug. 25, 2005

(30) Foreign Application Priority Data
Feb. 20, 2004    (DE) .......................... 10 2004 008 321

(51) Int. Cl.
*G01B 11/00*    (2006.01)
(52) U.S. Cl. ....... 264/409; 264/406; 264/40.1; 425/149; 425/164; 425/150
(58) Field of Classification Search .................. 264/409, 264/406, 40.1; 464/427; 250/339.07; 425/149, 425/167, 150
See application file for complete search history.

(56) References Cited

U.S. PATENT DOCUMENTS

| | | | | |
|---|---|---|---|---|
| 3,734,663 A * | 5/1973 | Holm | ............................. | 425/147 |
| 3,982,865 A * | 9/1976 | Adams et al. | .................. | 425/149 |
| 4,570,229 A * | 2/1986 | Breen et al. | .................... | 700/206 |
| 4,817,006 A * | 3/1989 | Lewis | ............................. | 700/206 |
| 5,023,850 A * | 6/1991 | Metts et al. | ...................... | 368/28 |
| 5,504,332 A * | 4/1996 | Richmond et al. | ........ | 250/339.12 |
| 5,760,399 A | 6/1998 | Trygstad | | |
| 5,838,571 A * | 11/1998 | Lewis | ............................. | 700/206 |
| 6,362,891 B1 * | 3/2002 | Axon et al. | ..................... | 356/433 |
| 6,451,228 B1 * | 9/2002 | Hinzpeter et al. | ............ | 264/40.1 |
| 6,606,574 B2 * | 8/2003 | Takanabe | .......................... | 702/84 |
| 6,676,863 B2 * | 1/2004 | Christiaens et al. | ............ | 264/39 |

(Continued)

FOREIGN PATENT DOCUMENTS
DE           697 00 834 T2      1/1997
(Continued)

OTHER PUBLICATIONS

R. Miller, "The Use of Near Infra Red Technology to Map Roller Compaction Processing Applications", IBA Proc Inst Briquet Agglom Conf, Nov. 1999, vol. 26, pp. 17-26.

(Continued)

*Primary Examiner* — Joseph S Del Sole
*Assistant Examiner* — David N Brown, II
(74) *Attorney, Agent, or Firm* — Clark & Brody

(57) ABSTRACT

A method for quality surveillance in manufacturing tablets in a rotary tablet press which, in a compression chamber, has a rotor with upper and lower rams, a die-plate, a cam system for the rams, at least one compressing station, and a charging system for the powdered material requiring compression wherein the tablets are checked for chemical and/or mechanical properties, wherein at least some chemical and/or mechanical data of the tablets is obtained by means of a NIR or LIF sensor in the compression chamber after the upper rams have left the dies, after a measuring procedure has been initiated by a machine computer in response to the die positions determined by a position generator relative to the NIR or LIF sensor.

16 Claims, 1 Drawing Sheet

U.S. PATENT DOCUMENTS

| | | | |
|---|---|---|---|
| 6,919,556 B1* | 7/2005 | Laurence | 250/222.2 |
| 2002/0125434 A1* | 9/2002 | Folestad et al. | 250/341.1 |
| 2003/0063279 A1* | 4/2003 | Lai et al. | 356/417 |
| 2004/0012781 A1* | 1/2004 | Gehrlein et al. | 356/328 |

FOREIGN PATENT DOCUMENTS

| | | |
|---|---|---|
| DE | 697 18 811 T2 | 11/1997 |
| EP | 0 431 269 B2 | 11/1998 |
| JP | 62-187598 | 8/1987 |
| JP | 4-47895 | 4/1992 |
| JP | 6-273318 | 9/1994 |
| JP | 9-206358 | 8/1997 |
| JP | 2000-258345 | 9/2000 |
| JP | 2003-519793 | 6/2003 |
| WO | 01/51915 | 7/2001 |

OTHER PUBLICATIONS

S. Han et al., "Determination of SB 216469-S during tablet production using near-infrared reflectance spectroscopy", *Journal of Pharmaceutical and Biomedical Analysis* 14, (1996) pp. 1681-1689.

C. Lai et al., "Nondestructive and On-line Monitoring of Tablets Using Light-induced Fluorescence Technology", *AAPS PharmSciTech* 2004; 5(1) Article 3 (http://www.aapspharmscitech.org).

* cited by examiner

METHOD AND APPARATUS FOR QUALITY SURVEILLANCE DURING THE MANUFACTURE OF TABLETS

FIELD OF INVENTION

The invention relates to a method for quality surveillance in manufacturing tablets in a rotary tablet press according to claim 1.

BACKGROUND OF THE INVENTION

Rotary tablet presses are generally known and are widely employed in the pharmaceutical industry. They have a rotor which usually is driven about a vertical axis of rotation, and upper and lower rams, dies, a die-plate and cam systems, and at least one compressing station. While the rotor rotates the cam system provides for the upper ram and lower ram to be positioned vertically on the graduated circle. The dies are filled with powdered material requiring compression by means of appropriate charging systems, e.g. an agitator blade device or a filling shoe by which the dies are continuously charged while the rotor rotates. Furthermore, the graduated circle of the rotor has disposed thereon preliminary and main pressure rollers by means of which the material requiring compression is compacted into a tablet. The tablets are ejected from the dies by means of the associated lower ram which is actuated by an ejector cam.

The tablets have to meet quality criteria. For example, they include the weight, hardness, break resistance, tablet height, active-substance content, active-substance release, dispersal, friability, porosity, surface, moisture content, etc. It is known to perform quality surveillance in a way that random sampling is done from the tablets produced. They are tested at a laboratory, using appropriate testing instruments. The manual effort and also time consumption is large. A major period of time will pass until process corrections are possibly made. When made by conventional measuring procedures (HPCL procedures), measurements of the quantitative fractions of active substances and additives will take hours or even days.

It also has been known already to carry out a so-called online process control. A suitable testing instrument is placed in the very vicinity of the tabletting machine. Random samples are taken automatically from the flow of tablets, are supplied to the testing instrument, are singularized and measured. This allows to automatically make an intervention in the process from the testing instrument to a machine computer via a computer interface. This procedure, which also helps test only a fraction of the tablets produced, only permits to check a few quality parameters, e.g. the weight, break resistance, and height. Another known procedure utilizes a measurement of the compression force for each individual tablet in the tablet press to check quality criteria. As is known the compression force is a measure for the tendency to fracture, tablet weight, and tablet hardness. A check of each tablet produced is possible here. However, a drawback is that this involves the use of an indirect measuring procedure which does not met with a full acceptance in the preparation prescriptions of the pharmaceutical industry. It does not detect important quality parameters such as the active-substance identity, active-substance content, dispersal, porosity, content of additives, etc.

BRIEF SUMMARY OF THE INVENTION

It is the object of the invention to indicate a method for quality surveillance in manufacturing tablets in a rotary tablet press that operates on-line, is adapted to check all tablets, and allows to detect a multiplicity of important quality parameters with no need to destroy the tablets.

The object is achieved by the features of claim 1.

In the inventive method, at least some chemical or mechanical property data of the tablets are obtained by means of at least one close-up infrared sensor or laser fluorescence sensor in the compression chamber after the upper rams leave the dies after a measuring procedure has been initiated by a machine computer in response to a die position determined by a position generator relative to the close-up infrared sensor or laser fluorescence sensor. The so-called close-up infrared spectroscopy (NIR) or laser fluorescence spectroscopy (LIF) is a measuring procedure, which is known as such, to determine properties of pharmaceutical substances including those of tablets. Its application necessitates a light or irradiation source and a receiver which records and transmits the desired data from the existing light or its spectrum.

In the inventive method, a measurement is made by means of NIR or LIF sensors within the compression chamber where it is made, after being assigned to the individual tablets or their positions, at a time after the rams of the press have compressed the tablet and the upper ram has left the die. However, it is necessary for the tablet to be still stationary relative to the die-plate and not to be located yet loosely on the surface of the die-plate. The sensor is able to detect the front-end face, for example, and also some portion of the cylindrical surface of the tablet in this area. The measuring process takes place either according to the reflection procedure or transmission procedure. The transmission procedure will cease to be applied whenever the tablet is too thick or has too large a diameter. As mentioned previously, the measuring procedure is initiated by the machine computer which exists anyway for the operation of the rotary tablet press.

A pulse generator arranged on the rotor shaft, for example, helps determine the position of the die at the circumference accurately up to the smallest angular degrees and, thus, also the position of each die with respect to the sensor. The values measured for each tablet, i.e. its frequency spectra, are recorded by the machine computer or a supplementary computer which is connected to the computer, and are evaluated according to known methods such as chemometrics. The results of measurements about the mechanical and/or chemical properties of the tablet, e.g. the active-substance identity and/or active-substance content and/or content of additives and/or density and/or hardness and/or break resistance and/or porosity and/or other relevant measurable quality parameters, are used to carry out and/or display and/or data log statistical calculations such as for mean values and/or standard deviations and/or stop the tablet press if the limit range is exceeded. Moreover, the statistical calculations may be employed for utilizing deviations of quality data from setpoints for an activation of closed-loop systems which contribute to optimizing processes within the machine. For example, deviations of quality data from setpoints, e.g. those for the active-substance content and/or density and/or hardness and/or break resistance and/or porosity, can be utilzed to carry out optimizations of machine setting parameters, e.g. the speed of the rotor and/or speed of the charging system and/or charging depth and/or height of tablet lands and/or measure of immersion depth.

According to an aspect of the invention, the powdered material requiring compression, before being compacted, is monitored already for quality relevant parameters such as active-substance identity and active-substance content and/or content of additives and/or moisture content and/or temperature. They can be displayed if deviations from the setpoint occur. The tablet press can be stopped if it leaves limit ranges. For this case, sensors may be mounted on the feed hopper, feed tube or charging system (filling shoe) themselves. The results of measurement provided to the machine computer or supplementary computer may either be displayed and/or data logged and/or may cause the machine to stop if a predetermined limit range is exceeded. Furthermore, they may be processed statistically and/or may be utilized to regulate the tablet press.

The invention allows for a measuring method which is rapid and non-destructive as compared to previously known quality control methods. It permits to check each individual tablet. However, it is also possible to check only some amount of the tablets. Since the results of measurement are available very quickly a rapid process optimization becomes possible by means of appropriate closed-loop systems. Another advantage is that the batch produced can be released immediately. In conventional methods, there is a more or less large interval of time between the manufacture and release of a batch. The invention makes it possible to interrupt the production process very early if the limit ranges of quality parameters are exceeded or while a batch is released. Process safety is enhanced altogether while process costs are simultaneously reduced. It is understood that, apart from the inventive method, a conventional sample measurement can be made that leads to precise results with regard to individual parameters.

BRIEF DESCRIPTION OF THE DRAWINGS

The invention will be described in more detail below with reference to the drawings.

DETAILED DESCRIPTION OF THE INVENTION

Figure 1:
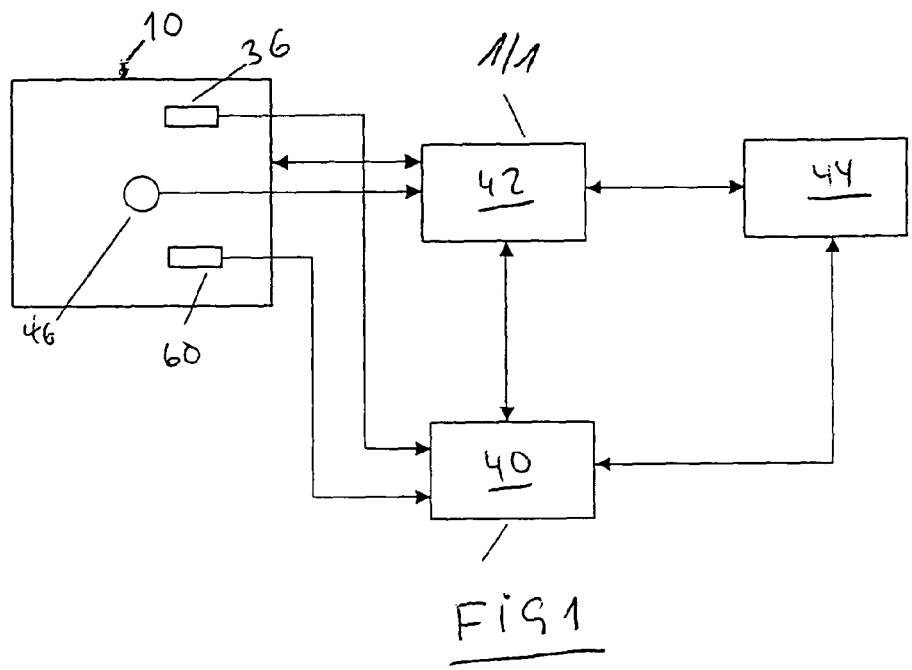
FIG. 1 shows a circuit arrangement of an apparatus for the implementation of the inventive method.
Figure 2:
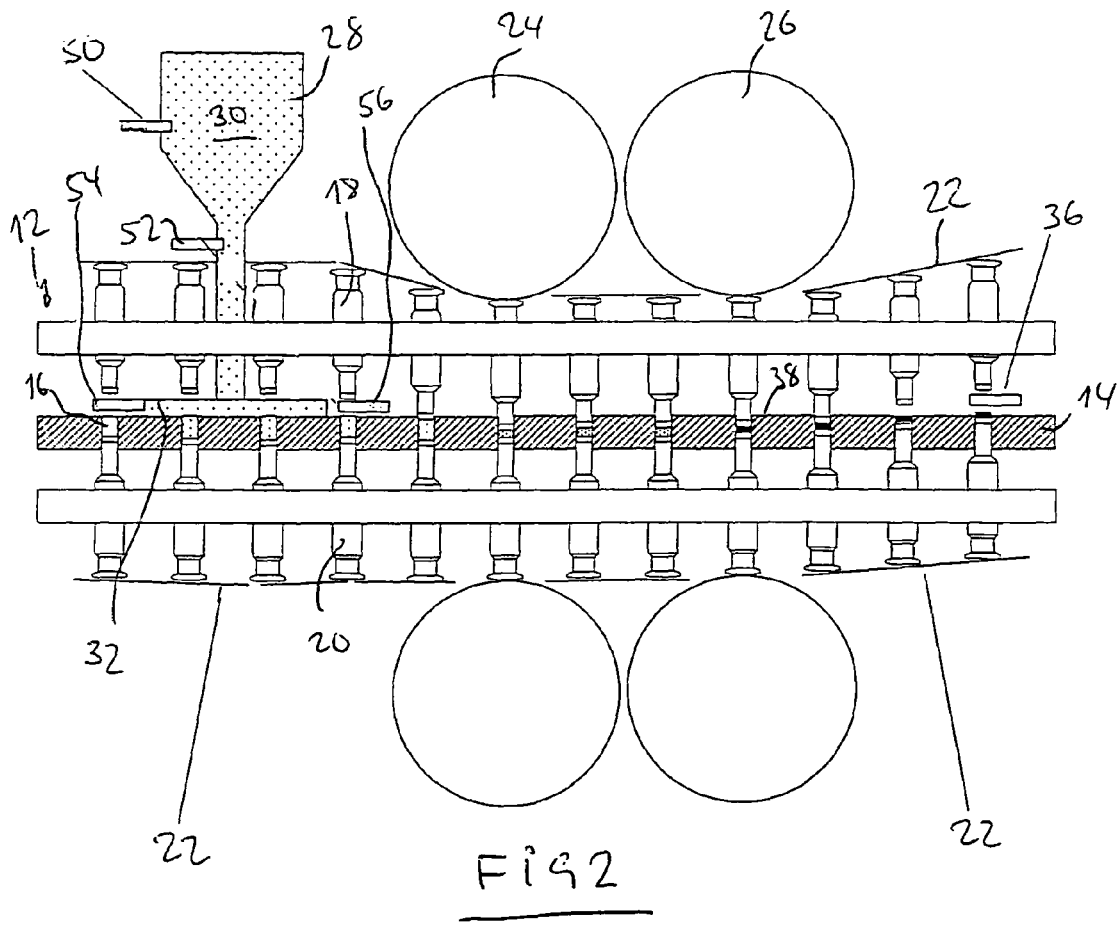
FIG. 2 shows a detail of a rotary tablet press in an apparatus according to the invention.

In FIG. 1, for example, a rotary tablet press is generally shown, i.e. the compression chamber of this machine the details of which will be briefly described later with reference to FIG. 2. In FIG. 2, some portion of a rotor 12 is shown which is rotatably driven about a vertical axis (not shown). The rotor has a die-plate 14 including individual dies 16 which have associated therewith a pair of compression rams each, namely an upper ram 18 and a lower ram 20. The compression rams 18, 20 interact with stationary cam elements 22 which predetermine the positions of the rams each while rotating with the rotor 12. A pair of preliminary pressure rollers 24 and a pair of main pressure rollers 26 is illustrated in FIG. 2. The pairs of pressure rollers 24, 26 use the help of the compression rollers, which run therebetween, to compact the powdered material as is knows as such. The powdered material is fed by means of a feed hopper 28 which supplies powdered material 30 to a filling shoe 32. The shoe successively charges the individual dies with a predetermined batch of powder, which batch of powder is determined by the position of the lower rams 20 in the dies 16. This is also known as such.

In FIG. 2, a NIR or LIF sensor 36 can further be seen which is stationarily disposed above the die-plate 14 and above the graduated circle of the dies 16. The way the sensor 36 is mounted is such that the respective upper ram has moved out of the die 16 already sufficiently far to provide sufficient space for the sensor 36. On the other hand, a tablet 38 which was compressed before is still within the die and, hence, still has a predetermined position.

As was explained previously such a sensor, which operates according to a procedure which is known as such, makes it possible to check a large series of quality criteria for the tablet.

FIG. 1 illustrates the sensor 36. It is located in the compression chamber of the tablet press 10 that also houses the elements shown in FIG. 2. The sensor 36 is connected to a computer 40 which, in turn, collaborates with a machine computer 42 for the tablet press. Such a machine computer is known in tablet presses for the control and regulation of their operation. The machine computer 42 cooperates with a service computer 44 which is also connected to the supplementary computer 40. The shaft of the rotor (not shown) has associated therewith a pulse generator 46 the signals of which are provided to the machine computer 42. The pulse generator 46, for example, is a known angle encoder which provides an appropriate signal to the machine computer 42 in small angular increments for a determination of the position of the individual dies 16 of the rotor 12 (FIG. 2). The data determined by the sensor 36 is evaluated in the supplementary computer 40 and is inputted to the machine computer 42 for an association with the individual tablets which have been compressed in the respective dies. Conversely, the machine computer 42 initiates a position-dependent evaluation procedure in the supplementary computer 40. The display of certain determined data is performed on the service computer 44.

As is apparent from FIG. 2 the tablet press has associated therewith more sensors. One sensor 50 is associated with the feed hopper 28 and another sensor 52 is associated with the charging tube from the hopper 28 to the filling shoe 32. The filling shoe 32 has associated therewith a sensor 54. A fourth sensor 50 is located directly after the filling shoe 32. Each of the sensors 50 to 56 which again are NIR or LIF sensors allows to check the powdered material 30 in the above-described manner.

The sensors 50 to 56 are combined into a sensor 60 for reasons of simplicity in FIG. 1. As is evident, the sensor 60 is also connected to the supplementary computer for an evaluation.

It is understood that any combination of the illustrated sensors may be implemented. Furthermore, any combination may be combined with conventional measurements.

The invention claimed is:

1. A method for quality surveillance in manufacturing tablets in a rotary tablet press which, in a compression chamber, has a rotor with upper and lower rams, a die-plate, a cam system for the rams, at least one compressing station, and a charging system for the powdered material requiring compression wherein the tablets are checked for at least chemical and/or mechanical properties, characterized in that at least some chemical and/or mechanical data of the tablets is obtained by means of a NIR or LIF sensor in the compression chamber after the upper rams have left the dies, wherein the NIR or LIF sensor is stationarily disposed above the die-plate and above a graduated circle of the dies and a tablet to be checked is still within the die, and further wherein the data is obtained after a measuring procedure has been initiated by a machine computer in response to the die positions determined by a position generator relative to the NIR or LIF sensor, wherein, if the obtained data deviates from set-points, at least one closed loop system is triggered to optimize machine settings including one or more of speed of the rotor, speed of the charging machine, charging depth, height of tablet lands, and a measure of immersion depth of the upper and lower rams.

2. The method according to claim 1, characterized in that properties of the powdered material requiring compression are checked within the compression chamber by means of a further NIR or LIF sensor.

3. The method according to claim 2, characterized in that the powdered material requiring compression is checked in a conduit leading to the charging system, within the charging system and/or in a die.

4. The method according to claim 1, characterized in that mean values or standard deviations are calculated from the data of the checked properties.

5. The method according to claim 1, characterized in that the tablet press is stopped if it exceeds limit values or limit ranges.

6. A rotary tablet press wherein a compression chamber has disposed therein a rotor with upper and lower rams, a die-plate, cam members for the rams, at least one compressing station, and a charging system for the powdered material, characterized in that a NIR or LIF sensor (36) is stationarily disposed in the compressing station above the die-plate (14) near a graduated circle of the dies (16), the NIR or LIF sensor obtaining at least chemical and/or mechanical properties of a tablet which is still within the die and connected to a machine computer (42) and/or a supplementary computer (40), and a shaft of the rotor (12) has associated therewith a pulse generator (46) for determining die positions relative to the NIR or LIF sensor, wherein said pulse generator is also connected to said machine computer (42) for an assignment of the sensor signals to position signals of the pulse generator (46), the machine computer adapted to initiate a measuring procedure to obtain data as the mechanical and/or chemical properties of the tablet in the die sensed by the NIR or LIF sensor in response to the determined die positions, the press further comprising at least one closed loop system which is triggered to optimize machine setting parameters, including one or more of speed of the rotor, speed of the charging machine, charging depth, height of tablet lands, and a measure of immersion depth of the upper and lower rams, if the data obtained by the NIR or LIF sensor deviates from set-points.

7. A rotary tablet press according to claim 6, characterized in that a further NIR or LIF sensor (50, 52, 54, and 56) which is connected to the machine computer (40, 42) is disposed on a feed hopper (30) and/or a charging system (32) and/or above the die-plate (14) near the charging system.

8. The method according to claim 2, characterized in that mean values or standard deviations are calculated from the data of the checked properties.

9. The method according to claim 3, characterized in that mean values or standard deviations are calculated from the data of the checked properties.

10. The method according to claim 2, characterized in that the tablet press is stopped if it exceeds limit values or limit ranges.

11. The method according to claim 3, characterized in that the tablet press is stopped if it exceeds limit values or limit ranges.

12. The method according to claim 4, characterized in that the tablet press is stopped if it exceeds limit values or limit ranges.

13. The method according to claim 1, wherein the step of checking for mechanical properties further comprises checking the tablets for physical properties and physical property data obtained is used for the triggering step.

14. The press according to claim 6, wherein the adaptation of the machine computer to obtain data as the chemical and/or mechanical properties obtains at least a physical property of the tablet in the die sensed by the NIR or LIF sensor.

15. The method according to claim 1, wherein at least a chemical property of the tablet is checked.

16. The press according to claim 6, wherein the adaptation of the machine computer to obtain data as the chemical and/or mechanical properties obtains at least a chemical property of the tablet in the die sensed by the NIR or LIF sensor.

* * * * *